United States Patent
Iwase

(10) Patent No.: US 8,615,115 B2
(45) Date of Patent: Dec. 24, 2013

(54) MEDICAL DIAGNOSIS OUTPUT DEVICE, METHOD, AND STORAGE MEDIUM THEREFOR

(75) Inventor: Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 741 days.

(21) Appl. No.: 12/504,952

(22) Filed: Jul. 17, 2009

(65) Prior Publication Data
US 2010/0034438 A1 Feb. 11, 2010

(30) Foreign Application Priority Data
Aug. 7, 2008 (JP) ................................. 2008-204774

(51) Int. Cl.
*G06K 9/00* (2006.01)
(52) U.S. Cl.
USPC ................................. 382/128; 705/3; 600/306
(58) Field of Classification Search
None
See application file for complete search history.

(56) References Cited

U.S. PATENT DOCUMENTS

| | | | |
|---|---|---|---|
| 6,108,635 A * | 8/2000 | Herren et al. ...................... 705/2 |
| 6,609,135 B1 * | 8/2003 | Omori et al. ............................ 1/1 |
| 6,904,161 B1 * | 6/2005 | Becker et al. .................. 382/128 |
| 2004/0165792 A1 * | 8/2004 | Bamberger et al. ............ 382/305 |
| 2005/0226593 A1 * | 10/2005 | Glassman et al. ................ 386/46 |
| 2006/0259505 A1 * | 11/2006 | Nodate et al. .................. 707/102 |
| 2007/0127793 A1 * | 6/2007 | Beckett et al. ................. 382/128 |
| 2008/0039707 A1 * | 2/2008 | Sugiyama et al. ............. 600/407 |
| 2008/0057478 A1 * | 3/2008 | Choi .............................. 433/215 |
| 2008/0154952 A1 * | 6/2008 | Waldinger et al. ......... 707/104.1 |
| 2008/0214907 A1 * | 9/2008 | Gutkowicz-Krusin et al. ............................. 600/306 |
| 2009/0060304 A1 * | 3/2009 | Gulfo et al. ................... 382/128 |

FOREIGN PATENT DOCUMENTS

| | | |
|---|---|---|
| JP | A 2003-099533 | 4/2003 |
| JP | A 2003-122849 | 4/2003 |
| JP | A 2003-288068 | 10/2003 |
| JP | A 2004-078299 | 3/2004 |
| JP | A 2006-318154 | 11/2006 |
| JP | A 2007-094471 | 4/2007 |

OTHER PUBLICATIONS

Richard A. Robb; Shmuel Aharon; and Bruce M. Cameron, "Patient-Specific Anatomic Models From Three Dimensional Medical Image Data for Clinical Applications in Surgery and Endoscopy", Aug. 1997, Journal of Digital Imaging, vol. 10, No. 3, Suppl. 1, pp. 31-35.*
PictureGear Lite Version 1.1 instruction manual, Sony Corporation. 1997, pp. 38, 39, 42, 43.
Office Action issued on Nov. 2, 2012, in counterpart Japanese Patent Application 2008-204774.

* cited by examiner

*Primary Examiner* — Samir Ahmed
*Assistant Examiner* — Siamak Harandi
(74) *Attorney, Agent, or Firm* — Fitzpatrick, Cella, Harper & Scinto

(57) ABSTRACT

An output device that outputs a schematic view showing a position of a diseased part of a human body, comprises: a read-out unit adapted to read out a plurality of schematic views output from a storage unit adapted to store the schematic views, and a control unit adapted to output the plurality of schematic views read out by the read-out unit to an output unit, wherein the read-out unit selects a schematic view to be read out based on an output format that has been set by a user.

18 Claims, 12 Drawing Sheets

FIG. 7A
FIG. 7B
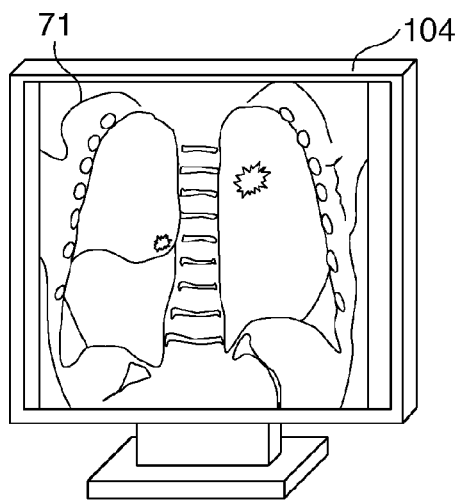
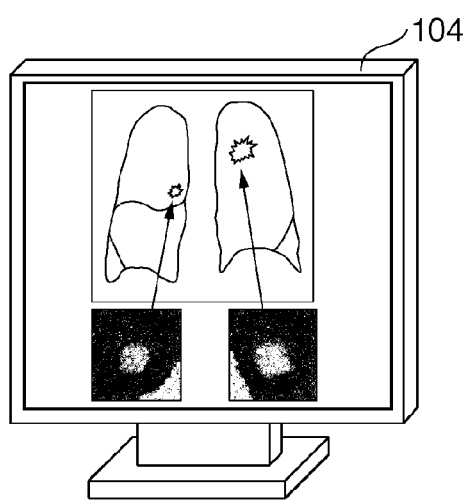

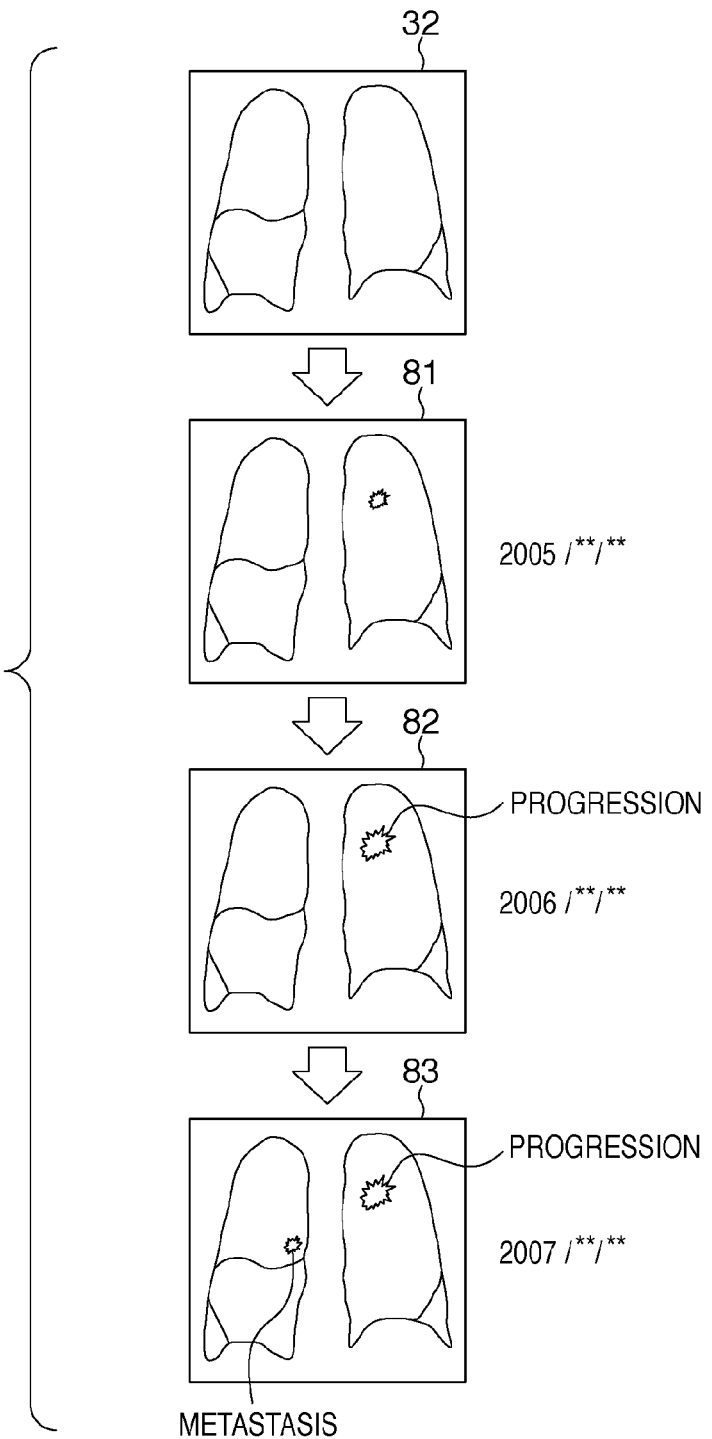
F I G. 8

MEDICAL DIAGNOSIS OUTPUT DEVICE, METHOD, AND STORAGE MEDIUM THEREFOR

BACKGROUND OF THE INVENTION

1. Field of the Invention

The present invention relates to an output device, a method, a program, and a storage medium therefor, and particularly to a diagnosis support technique for creating a medical document, such as a chart (medical record) or an image diagnosis report. In particular, the present invention relates to a technique for outputting a schematic view (schema) showing a positional relationship between a human body structure and a diseased part that a doctor draws on a medical document.

2. Description of the Related Art

Before medical documents, such as charts or image diagnosis reports, were computerized, a doctor drew a schema (a schematic view showing a positional relationship between a human body structure and a diseased part) by hand on a medical document made from paper. Recently, as medical information systems such as HIS or PACS have become widely used, the computerization of such medical documents has been gradually introduced. That is, a medical document, such as a chart or an image diagnosis report, conventionally created by a doctor by hand is electronically created and displayed using an information device, and moreover a diagnosis support device that enables communication with another medical information system has come into use. Note that "HIS" is an abbreviation for Hospital Information System, and "PACS" is an abbreviation for Picture Archiving and Communication System.

When electrically creating a medical document, a character string can be comparatively easily input using a keyboard. On the other hand, in order to draw a diagram having an arbitrary shape, by operating an input device such as a mouse or a tablet, it is possible to input a trajectory drawn by the input device as line information. However, since it is necessary to precisely draw a human body structure having a complex shape when creating a schema, it is not easy to draw a diagram satisfying the necessary requirements with a drawing method using a mouse or a tablet.

In view of this, Japanese Patent Laid-Open No. 2006-318154 discloses a configuration in which a plurality of schema templates (hereinafter, referred to as basic schemata) are previously stored in a device, and a doctor is allowed to select a desired basic schema. Using this configuration, after selecting a basic schema, the doctor can create a schema by drawing a simple diagram showing a diseased part on a basic schema (hereinafter, a basic schema on which a diagram showing a diseased part has been drawn is referred to as a schema).

Further, a configuration in which a desired schema out of a plurality of schemata created as described above is displayed on a monitor is known. Japanese Patent Laid-Open No. 2003-122849 describes a configuration in which shortcuts such as a name of disease and a syndrome are provided on a screen of an electronic chart so that a doctor can obtain desired information by selecting these shortcuts.

However, the conventional configurations have the following problems.

Although the configuration described in Japanese Patent Laid-Open No. 2003-122849 allows the call-out of a schema drawing from a shortcut associated with a disease name or the like, it is necessary for a doctor to designate a disease name or the like in order to call out a desired schema drawing from a plurality of schema drawings. Here, since a great number of disease names that can be designated exist, it is troublesome to perform an operation for designating a disease name and calling out a schema drawing with such a conventional configuration.

Further, as for a schema having information indicating changes with the passage of time or dynamic information, when displaying such a schema on a monitor, since information pieces can be switched and displayed, a doctor can check a plurality of information pieces. However, a great number of schemata that are display targets exist; thus, it was troublesome for a doctor to perform an operation for selecting a schema to be displayed.

SUMMARY OF THE INVENTION

The present invention has been achieved in view of the above problems and aims to provide a technique which enables automatic selection of only a necessary schema from a great number of schemata and output by performing an easy operation.

According to one aspect of the present invention, an output device that outputs a schematic view showing a position of a diseased part of a human body, comprises:
  a read-out unit adapted to read out a plurality of schematic views output from a storage unit adapted to store the schematic views, and
  a control unit adapted to output the plurality of schematic views read out by the read-out unit to an output unit,
  wherein the read-out unit selects a schematic view to be read out based on an output format that has been set by a user.

According to another aspect of the present invention, an output method performed by an output device that outputs a schematic view showing a position of a diseased part of a human body, the method comprises:
  a read-out step of reading out a plurality of schematic views output from a storage unit adapted to store the schematic views, and
  a control step of outputting the plurality of schematic views read out in the read-out step to an output unit,
  wherein in the read-out step, the schematic view to be read out is selected based on an output format that has been set by a user.

Further features of the present invention will become apparent from the following description of exemplary embodiments with reference to the attached drawings.

BRIEF DESCRIPTION OF THE DRAWINGS

FIGS. 7A and 7B are diagrams showing examples of selected schemata.

FIG. 8 is a diagram showing an example case of dynamically outputting a plurality of schemata.

DESCRIPTION OF THE EMBODIMENTS

Hereinafter, the embodiments according to the present invention will be described in detail with reference to the attached drawings. A diagnosis support device (display device) in the embodiments of the present invention selects a changing state to be shown on a schematic view, alters/converts the displayed content for the changing state regarding a partial region with a method in accordance with an output format, and presents a doctor with the resulting content. It should be noted, however, that the constituent elements described in the following embodiments are merely exemplary, and are not intended to limit the scope of the present invention. It should also be noted that all the combinations of the features described in the present embodiments are not necessary to solve the problems of the present invention.

First Embodiment

Medical Diagnosis Support System

Figure 1:
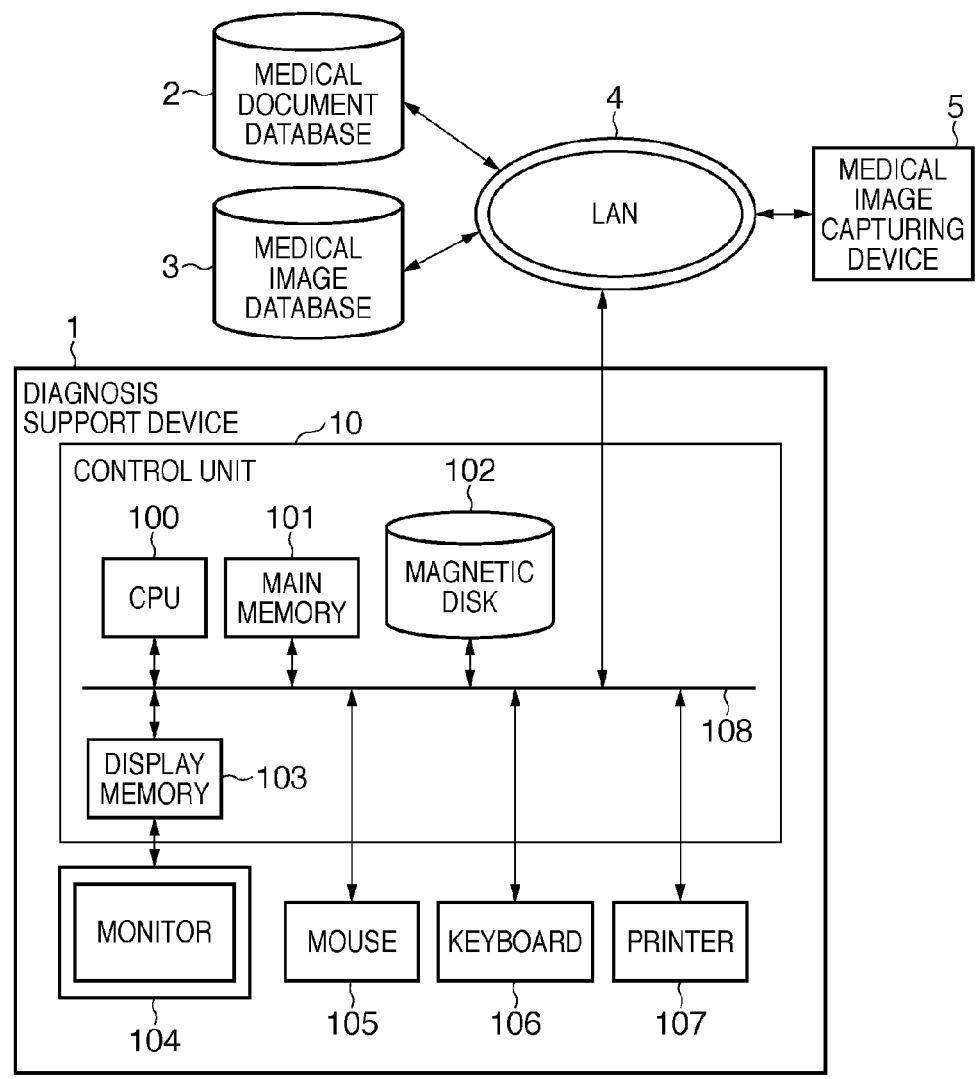
FIG. 1 is a diagram showing an example device configuration of a medical diagnosis support system.

FIG. 1 is a diagram showing an example device configuration of a medical diagnosis support system according to a first embodiment. In FIG. 1, a (medical) diagnosis support device 1 has a control unit 10, a monitor 104, a mouse 105, a keyboard 106, and a printer 107. The control unit 10 has a central processing unit (CPU) 100, a main memory 101, a magnetic disk 102, and a display memory 103. Further, by the CPU 100 executing programs stored in the main memory 101, communication with a medical image capturing device 5 or a medical image database 3, and various controls such as overall control of the medical diagnosis support device 1 can be executed.

Also, as shown in FIG. 1, the medical diagnosis support device 1 is connected to the medical image capturing device 5, which can capture an image of a subject. Examples of the medical image capturing device 5 include, for example, an X-ray CT device, an MRI device, an ultra-sound device, an X-ray device, a nuclear medicine device, and the like. Furthermore, the medical diagnosis support device 1 may be configured so as to be connected to the medical image database 3, which stores medical images captured by the medical image capturing device 5 and medical examination data including information necessary for diagnosis support processing, and the like, so as to obtain a necessary medical image and the like therefrom.

The CPU 100 mainly controls operations of constituent elements of the medical diagnosis support device 1. A RAM (Random Access Memory) can realize the main memory 101, which stores control programs executed by the CPU 100, provides a work area when the CPU 100 executes a program, and so on. The magnetic disk 102 stores an operating system (OS), device drivers for peripheral devices, various applications software including programs for performing diagnosis support processing (described later) and the like, and so on. The display memory 103 temporarily stores display data to be displayed on the monitor 104. For example, a CRT monitor, a liquid crystal monitor, and the like can be used as the monitor 104, which displays an image based on data from the display memory 103. The mouse 105 and the keyboard 106 respectively input pointing input, and the input of characters, and the like in response to a user operation. The printer 107 prints texts and images. The aforementioned constituent elements are connected via a common bus 108, which enables the elements to communicate with each other.

In the present embodiment, the medical diagnosis support device 1 can read out medical image data and the like from the medical image database 3 via a LAN 4. Alternatively, the medical diagnosis support device 1 may be connected to a storage device such as, for example, an FDD, a CD-RW drive, an MO drive, or a ZIP drive, and may read medical image data and the like from such a drive. Also, the medical diagnosis support device 1 may directly obtain a medical image and the like from the medical image capturing device 5 via the LAN 4.

Diagnosis Support Processing

Figure 2:
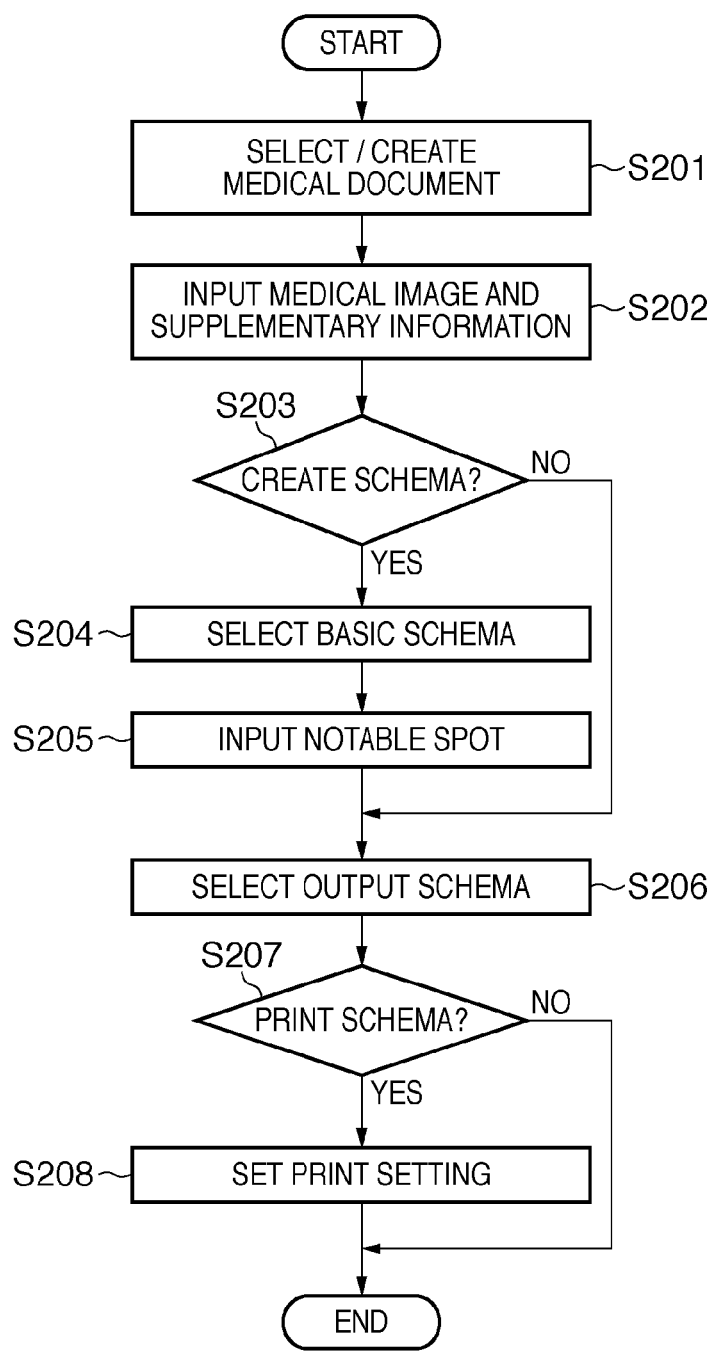
FIG. 2 is a flowchart showing steps in a diagnosis support process executed by a diagnosis support device 1.
Figure 3A:
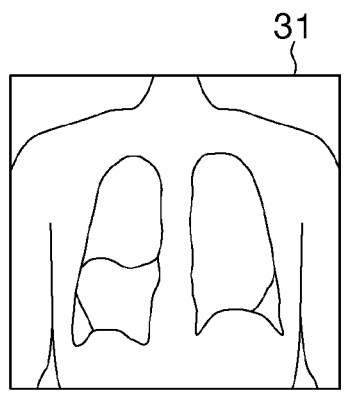
FIGS. 3A, 3B, 3C, 3D, 3E, and 3F are diagrams showing examples of basic schema candidates.
Figure 3B:
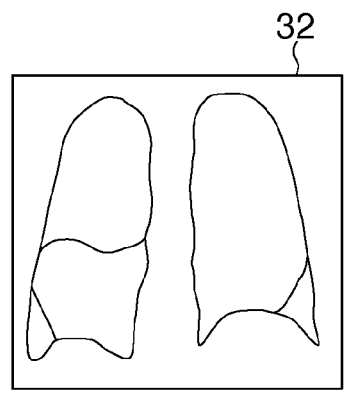
Figure 3C:
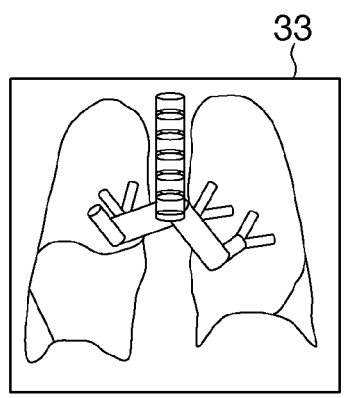
Figure 3D:
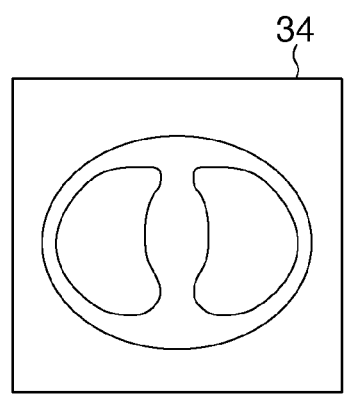
Figure 3E:
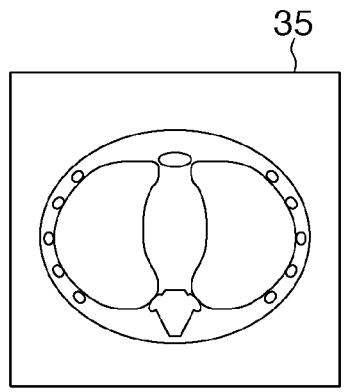
Figure 3F:
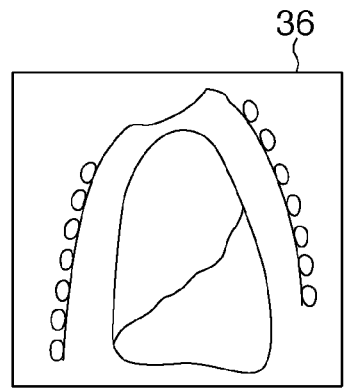

Next, with reference to a flowchart shown in FIG. 2, how the control unit 10 controls the medical diagnosis support device 1 will be described. FIG. 2 is a flowchart showing steps in a diagnosis support process executed by the diagnosis support device 1. Note that the processing shown by the steps of the flowchart shown in FIG. 2 is realized by the CPU 100 executing programs stored in the main memory 101. Steps of a process performed when medical image data including a captured image such as a diseased part, and the like is read, a user creates a schema, and an electronic chart on which a schema is recorded is printed will be described below. Note that a case in which a doctor operates the present configuration as a user will be described below.

In step S201, the CPU 100 performs processing for inputting desired medical image data into the medical diagnosis support device 1 in accordance with input from the mouse 105 or the keyboard 106. Hereinafter, medical image data input in step S201 will be referred to as a diagnostic image. In the processing for inputting image data, for example, as described above, the CPU 100 receives medical image data as a diagnostic image via the LAN 4 from the medical image database 3, which saves captured medical image data. Alternatively, the CPU 100 reads image data as a diagnostic image from a storage device connected to the medical diagnosis support device 1, that is, for example, various types of a storage medium, such as an FDD, a CD-RW drive, an MO drive, or a ZIP drive.

In step S202, in accordance with a command input from a doctor, the CPU 100 reads, into the main memory 101, a medical image and supplementary information, and a medical document on which the course of medical examinations and the like are recorded. Reading of a medical image and supplementary information can be realized by the CPU 100 communicating with the medical image database 3 via the common bus 108 and the LAN 4 so as to receive a desired medical image and supplementary information. Alternatively, reading of a medical image and supplementary information can be realized by the CPU 100 reading a desired medical image and supplementary information from an external storage device connected to the diagnosis support device 1.

Supplementary information herein is information indicating, for example, the type of an imaging device that captured a medical image, imaging conditions, the region of a human body that was an imaging target, and so on, and can be provided, for example, in a text format. Such supplementary information is generated by the medical image capturing device 5, and saved in the medical image database 3 in association with a medical image at the same time as the image is captured.

As for treating such information, a communication protocol dedicated for medical image data is being standardized, which enables an image diagnosis device, a medical information server, and further still a medical information viewer that are manufactured by different manufacturers to communicate with each other. For example, the DICOM (Digital Imaging and Communications in Medicine) standard has been established.

Reading of a medical document can be realized by the CPU 100 communicating with a medical document database 2 via the common bus 108 and the LAN 4 so as to receive a desired medical document. Here, a medical document to be received is, in the case of a patient taking a wait-and-see approach, a medical document that was last saved when the patient was diagnosed last time, and in the case of a new patient, is a medical document in which a patient attribute, such as a name, gender, a birth date of the patient, has been input.

The CPU 100 reads out a diagnostic image and a medical document, which have been read, from the main memory 101, and outputs these to the monitor 104.

In step S203, selection of whether to create a schema is received from the doctor. If the doctor selects to create a schema (YES in step S203), the processing proceeds to step S204, and the CPU 100 presents a basic schema selection list to the doctor. If the doctor does not select to create a schema (NO in step S203), the processing proceeds to step S206.

In step S204, selection of a basic schema is received from the doctor. The CPU 100 reads out a great number of basic schemata stored on the magnetic disk 102, and displays a schema list that is a list thereof on the monitor 104.

An identification name and an identifier, which enable identification of a basic schema group and an individual basic schema, are assigned to a basic schema stored on the magnetic disk 102. Here, basic schema groups are groups divided into units such as the head/cervical region, the lungs, the heart/circulatory organ, the digestive system, the bones, or the ear, nose, and throat. Further, such a group is hierarchical and, for example, in the case of a group for the lungs, the group is further divided into units such as the lungs (front side) or the lungs (lateral side). An identification name is used when a doctor distinguishes between types of basic schemata, and has a name such as "lung (front side)", or "head (left lateral side)". An identifier is used when the CPU 100 distinguishes between types of basic schemata, and is represented in bits such as "100000000001" or "001000100100". Using such an identifier, the CPU 100 identifies a group and type of a basic schema. Here, it is sufficient if the CPU 100 can distinguish between types of basic schemata; thus, an identifier is not limited to a number of bits or a bit representation.

A schema list to be output onto the monitor 104 may be a list in which identification names of basic schemata are enumerated or a list in which thumbnail images (images reduced to a size suitable for displaying in a list) of basic schemata are enumerated. Also, a schema list may be hierarchically grouped and sequentially displayed from a grouped list at the top in the hierarchy. When the doctor selects a desired basic schema from the schema list displayed on the monitor 104, the CPU 100 reads the selected basic schema into the main memory 101.

Another method for selecting a basic schema is a method with which the CPU 100 may automatically select basic schema candidates from supplementary information read in step S202 and present the candidates to the doctor, and then the doctor may select a schema from the candidates. For example, the CPU 100 reads out information regarding an imaging device and a region whose image has been captured from supplementary information. Then, if the imaging device is a CT device and the region whose images have been captured is the chest, as shown in FIGS. 3A, 3B, 3C, 3D, 3E, and 3F, basic schema candidates are shown along three orthogonal cross sections as coronal images 31 to 33, axial images 34 and 35, and a sagittal image 36; thus, basic schemata that have different levels of detail are the candidates. If the imaging device performs plain radiography, the basic schema candidates are the frontal (coronal) images 31 to 33. Note that FIGS. 3A, 3B, 3C, 3D, 3E, and 3F are diagrams showing examples of basic schema candidates.

Next, in step S205, the doctor performs processing for inputting a notable spot on a diagnostic image into a basic schema. That is, processing in which the setting of a notable spot on a diagnostic image in a basic schema is received from the doctor is performed.

This processing can be realized by performing processing in which, for example, the doctor designates, on a basic schema, a spot that may be a diseased part on the diagnostic image using the mouse 105, the keyboard 106, a diagrams tablet (not shown), or the like, so as to input that information in the diagnosis support device 1. Designation of a notable spot can be executed, for example, using a method with which image coordinates are input as a point, a method with which a set of image coordinates or information as an alternative thereto is input as information regarding a region on an image, a method with which a template is selected from a great number of templates stored on a magnetic disk 102 and input, or the like. Further, the number of notable spots designated by a doctor may not be limited to only one with respect to the diagnostic image, and the input of a plurality of points, a plurality of regions, or the like with respect to a basic schema may be received. For example, there is a case in which a spot considered to be a primary spot of a disease and a spot where the disease may have metastasized are designated as notable spots. In this case, processing for successively storing a plurality of designated notable spots can be performed, and the doctor can input a command indicating that input of notable spots is finished.

Figure 4A:
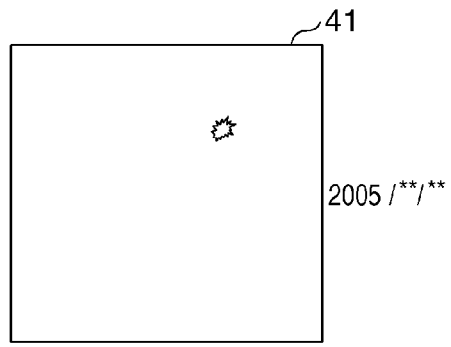
FIGS. 4A, 4B, 4C, and 4D are diagrams illustrating a schema and layers.
Figure 4B:
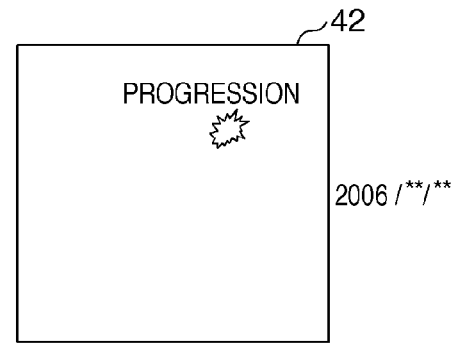
Figure 4C:
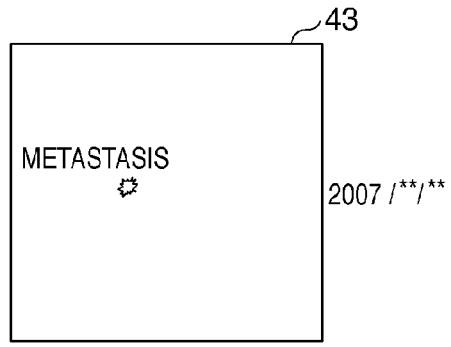
Figure 4D:
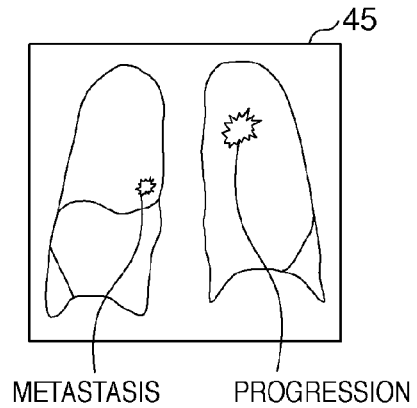

As shown in FIGS. 4A, 4B, and 4C, spots designated on a basic schema are saved on separate layers 41 to 43 in date units or in operation units. Note that FIGS. 4A, 4B, 4C, and 4D are diagrams illustrating a schema and layers. Further, a layer indicates a transparent image virtually provided, and in the present embodiment, a layer on which the doctor has drawn is superimposed on a basic schema so as to create a schema. For example, when a schema is newly created, the CPU 100 creates a layer at the same time when reading a basic schema 32 (FIG. 3B), and saves a notable spot designated by the doctor on the layer. Similarly, also when a new notable spot is designated on an existing schema created in the past, the CPU 100 creates a layer at the same time when reading the existing schema, and saves a notable spot designated by the doctor on the layer. A schema 45 (FIG. 4D) is created by combining the basic schema 32 and the layers 41 to 43.

A layer is created not only when reading a basic schema and reading an existing schema, and it is also possible that a new layer can be explicitly added at an arbitrary point in time when a doctor desires. Thereby, a plurality of different information pieces can be saved on one basic schema.

In the present embodiment, an example of processing in which the selection of a basic schema is received in step S204, and a notable spot is designated on a selected basic schema in step S205 is described. However, a method for designating a notable spot on a basic schema is not limited to this. For example, in accordance with the doctor designating a notable spot on a diagnostic image, the CPU 100 may automatically select and display a basic schema, and the doctor may designate the notable spot on the basic schema. Alternatively, in accordance with the doctor designating a notable spot on a diagnostic image, the CPU 100 may automatically select a basic schema, and the CPU 100 may automatically designate the notable spot on the basic schema. At this time, the CPU 100 adjusts the positions of the diagnostic image and the basic schema so that the notable spot that the doctor has designated on the diagnostic image corresponds to the notable spot to be designated on the basic schema.

In step S206, the selection of a schema output format is received from the doctor; thereafter, the CPU 100 selects a schema to be output in the output format selected by the doctor and outputs the schema onto the monitor 104. In this process, the selection of whether to output a plurality of schemata statically or dynamically is received. Note that in the case of statically outputting a plurality of schemata, a display region of the monitor 104 is divided so that a plurality of schemata are simultaneously displayed, and in the case of dynamically outputting a plurality of schemata, schemata to be displayed are automatically switched at an arbitrary timing and sequentially displayed one-by-one.

Figure 5A:
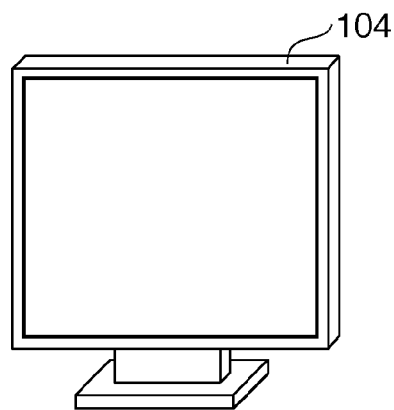
FIGS. 5A, 5B, and 5C are diagrams showing examples of divided display screens.
Figure 5B:
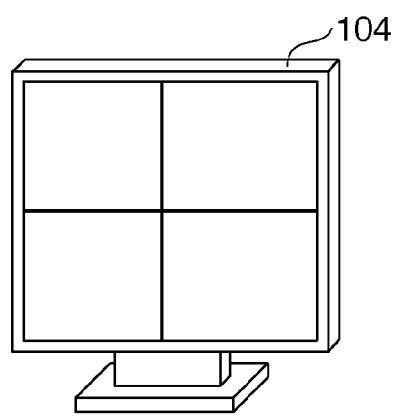
Figure 5C:
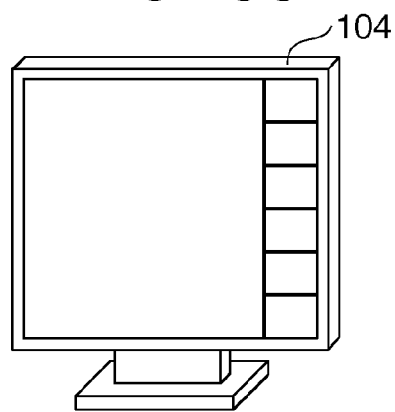

In the case of statically outputting a plurality of schemata onto the monitor 104, as shown in FIGS. 5A, 5B, and 5C, a display screen configuration is selected. FIGS. 5A, 5B, and 5C are diagrams showing examples of divided display screens. Accordingly, a number m, which is the greatest number of schemata to be displayed, can be set. Here, FIG. 5A is an example of a full screen display, FIG. 5B is an example of a divided display, and FIG. 5C is an example of a full screen display with thumbnail-displayed other candidates. In the case of FIG. 5C, a schema displayed on the full screen and a thumbnail-displayed schema can be controlled so as to be replaceable by performing drag-and-drop processing or the like using the mouse 105.

Figure 6:
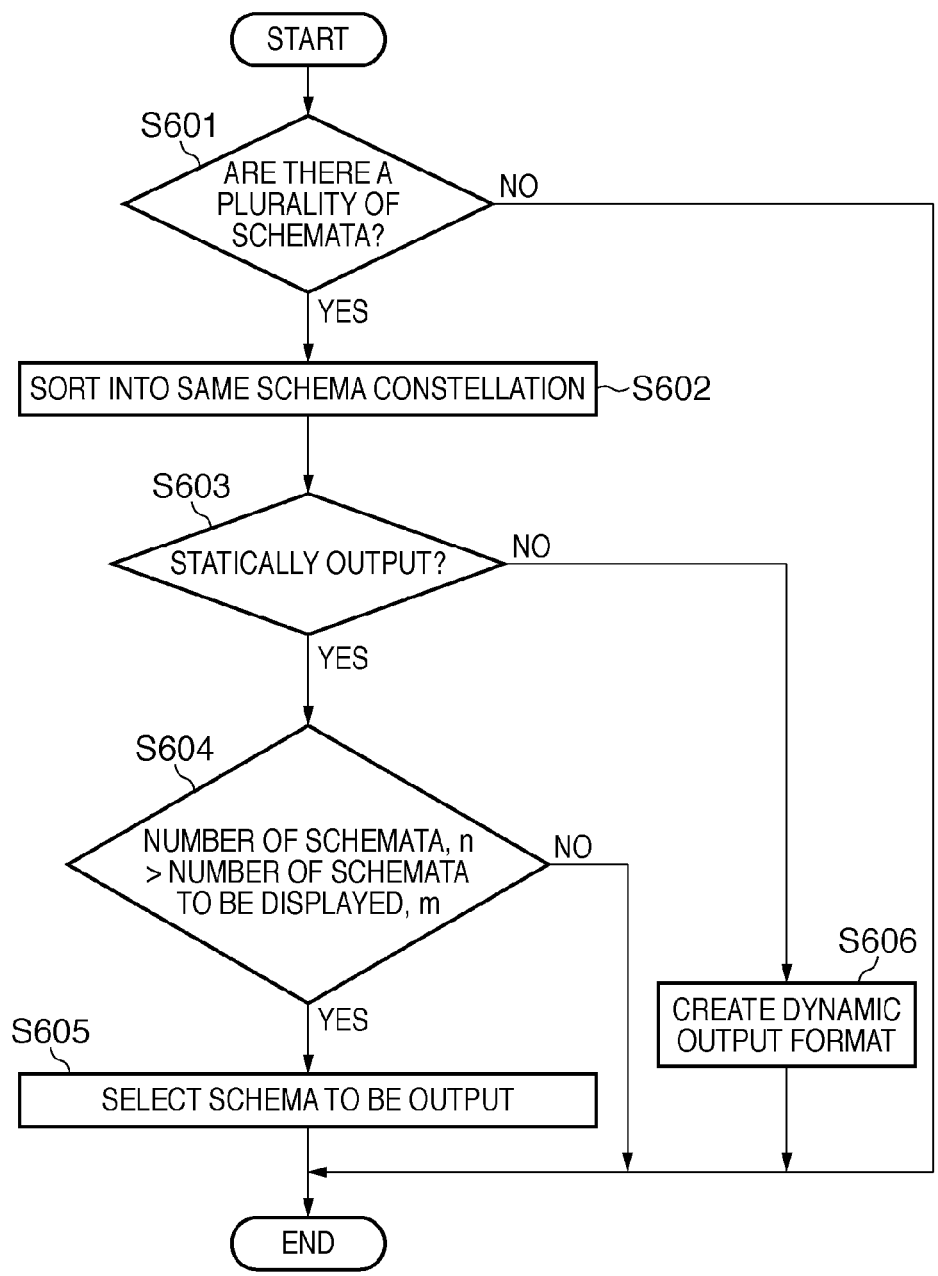
FIG. 6 is a flowchart showing steps of a process for selecting a schema to be output.

A specific processing procedure performed in step S206 will be described in detail with reference to FIGS. 6, 7A, 7B, and 8. FIG. 6 is a flowchart illustrating the detailed steps of a process performed in step S206.

First, in step S601, it is determined whether there is a plurality of schemata for the same patient. Hereinafter, the number of schemata for the same patient is referred to as the number of schemata. Thereafter, from a medical document read in step S202, the number of schemata created in the past and layers included therein is counted. At this time, the schemata created in each department, such as a department of surgery, a department of internal medicine, or a department of ophthalmology, are individually counted. Then, the number of schemata created in a department where the patient is diagnosed at this point is assumed to be n'. The number of schemata newly created in steps S204 and S205 and layers included therein is counted, and the resulting number and the number n', which is the number of schemata created in the past, are summed up. Consequently, the number n, which is the number of schemata (including the number of layers) created for the same patient can be obtained. In this case, for example, if one basic schema has one layer thereon, the counted number of schemata is one. If one basic schema has three layers thereon, the counted number is three. Consequently, it can be determined whether there is a plurality of schemata for the same patient. If there is a plurality of schemata for the same patient (YES in step S601), the processing proceeds to the next step S602.

In step S602, the CPU 100 divides a plurality of schemata created for the same patient into groups based on identifiers. Since an identifier is assigned to a basic schema, the CPU 100 can divide a schema image data constellation that has already been created into groups such as, for example, the lungs—the lungs (front side) and the lungs—the left lung (lateral side), based on the identifiers.

Next, in step S603, the selection of whether to output schemata statically or dynamically is received from the doctor. Then, the CPU 100 switches the processing depending on whether the schemata are to be output statically or dynamically. When schemata are statically output (YES in step S603), the processing proceeds to step S604, and when schemata are dynamically output (NO in step S603), the processing proceeds to step S606. Furthermore, in the case of statically outputting schemata, the setting of the number m, which is the greatest number of schemata to be displayed and output onto a monitor, is received. First, processing for statically outputting schemata, or in other words, steps S604 and S605 will be described.

In step S604, the CPU 100 compares the number n, which is the number of schemata created for the same patient, to the number m, which is the greatest number of schemata to be displayed and output. The number n, which is the number of schemata, is obtained in step S601, and the number m, which is the greatest number of schemata to be displayed, is set in step S603. Here, if the number n, which is the number of schemata, is greater than the number m, which is the greatest number of schemata to be displayed (YES in step S604), the processing proceeds to step S605. If the number n, which is the number of schemata, is equal to or less than the number m, which is the greatest number of schemata to be displayed (NO in step S604), the steps in FIG. 6 end, and the processing proceeds to step S207.

In step S605, the CPU 100 selects a number of schemata, m, out of the number of schemata, n. As a method for selecting the m number of schemata, for example, it is possible to select schemata related to a diagnostic image displayed on the monitor 104 at this time. For example, as shown in FIGS. 7A and 7B, when a chest CT image 71 is being diagnosed, a schema of the lungs or the heart/circulatory system related to the chest can be selected from a plurality of schemata image data constellations, and displayed. Note that FIGS. 7A and 7B are diagrams showing examples of selected schemata. At this time, since a diagnostic image includes notable spots, and an identifier is assigned to a basic schema, the CPU 100 can display a schema related to the diagnostic image that the doctor is displaying on the monitor 104. Here, a medical image corresponding to a schema or a partial region image of a changing portion in a medical image may be selected and displayed together with the schema at the same time. Thereafter, on ending processing in FIG. 6, the processing proceeds to step S207 in FIG. 2.

Next, in step S606, the case of dynamically outputting a plurality of schemata is described. As a dynamic output method, a case in which, for example, a notable spot is designated on a schema regarding the chest and, in order to further record detailed information, a notable spot is also designated on a detailed schema of the lungs is described. First, an entire region image regarding the chest is displayed so as to show an entire image and then is switched, in order to zoom in, to a partial region image of the lungs, which is then displayed.

If there are a plurality of layers on one basic schema, as shown in FIG. 8, the CPU 100 chronologically rearranges schemata in a schema constellation sorted in step S602 and selects a schema related to a diagnostic image displayed on the monitor 104 from the schema constellation. Note that FIG. 8 is a diagram showing an example case of dynamically outputting a plurality of schemata. Further, the CPU 100 outputs selected schemata onto the monitor 104 by chronologically switching layers on the basic schema 32 at an interval of a predetermined time t as shown in FIG. 8. Moreover, the CPU 100 also outputs the date when a notable spot was designated on a layer together with the layer. Consequently, even when coordinate positions of notable spots are in the same region on the layers, when a change occurred, or in other words, a change in the course of a disease is explicitly indicated.

Other than displaying one group in the schema constellation by chronologically switching schemata in the group, not only a schema constellation created in the same department, but also a plurality of schemata constellations for the same region may be chronologically displayed in the order of a hierarchical relationship. The same region corresponds to the highest level in the hierarchy of a basic schema list indicated in the description of step S204, such as the head/cervical region, the lungs, the heart/circulatory organ, or the digestive system. For example, as for a schema constellation for the abdomen, by switching and displaying schema constellations created in a plurality of departments, such as a department of internal medicine and a department of gastroenterology, even if a plurality of doctors individually created a schema, it is possible to check schemata regarding the same region in chronological order at one time.

Here, in the aforementioned case, selection of a medical image corresponding to a schema, or a partial region image of a changing portion in a medical image may be received, and the selected image may be simultaneously displayed together with the schema. By performing processing as described above, the selection of a schema output format is received from the doctor, and then, the CPU 100 selects a schema to be output in the output format selected by the doctor and outputs the schema onto the monitor 104. After that, on ending the processing in FIG. 6, the processing proceeds to step S207 in FIG. 2.

Referring back to FIG. 2, description is given thereon. On ending the processing in step S206, which has been described in detail with reference to FIG. 6, the selection of whether or not to perform processing for printing a schema is received from the doctor in step S207. When print processing is performed (YES in step S207), the processing proceeds to step S208, and when print processing is not performed (NO in step S207), the processing ends.

Figure 9:
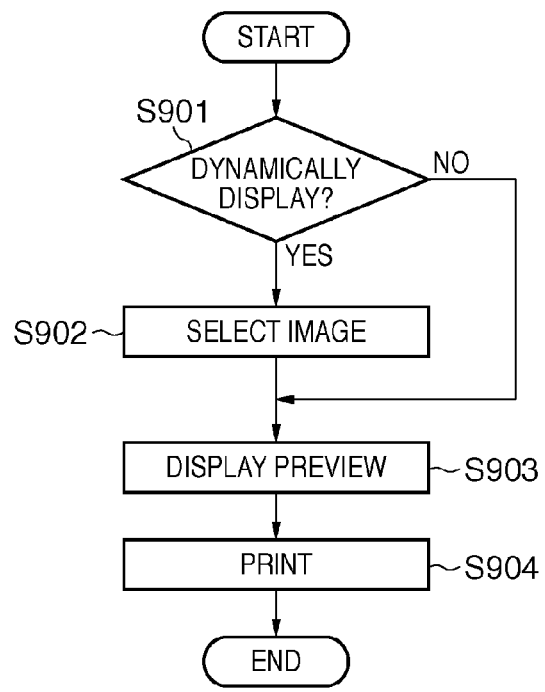
FIG. 9 is a flowchart showing steps of a process performed when printing a schema.

In step S208, the CPU 100 determines a schema output format and sets a print setting. Here, a specific processing procedure performed in step S208 will be described in detail with reference to FIG. 9. FIG. 9 is a flowchart showing the steps of a process performed when printing a schema.

First, in step S901, the CPU 100 determines whether a schema displayed on a monitor is dynamically output. When the schema is dynamically output (YES in step S901), the processing proceeds to step S902, and when the schema is not dynamically output (NO in step S901), the processing proceeds to step S903.

In step S902, the CPU 100 statically expands a schema image data constellation that is being dynamically output and selects a schema to be output from the expanded schema image data constellation. For example, the CPU 100 selects a combination of a basic schema and layers in date units, arranges them in chronological order, and outputs them.

Alternatively, the CPU 100 may chronologically output schemata created by superimposing a plurality of layers onto a basic schema. For example, as for the superimposition of a plurality of layers, when an exclusive disjunction A' xor B' of an area A' of a changing region designated on a layer A, and an area B' of a changing region designated on a layer B, is a fixed threshold value T or less, such layers are superimposed and displayed on the same basic schema. Such a process is repeatedly performed in chronological order, and if there is a layer N, whose exclusive disjunction is greater than the threshold value T, the layer N may be superimposed on a new basic schema. As a further alternative, the CPU 100 may select and display only a specific schema.

As a method for selecting a specific schema, it is possible that an image analyzing unit performs image analysis with respect to a diagnostic image, and thereafter a schema created when the amount of change of a changing region is greatest is selected and output together with the diagnostic image. Alternatively, as a method for selecting a specific schema, the CPU 100 may measure the time for which the doctor displayed a schema on the monitor 104 when diagnosing, and may select a schema based on the length of the display time.

In step S903, the CPU 100 displays a schema image selected to be printed on the monitor 104 as a preview image so as to enable the doctor to check the image.

Next, in step S904, the CPU 100 reads out an electronic chart together with a schema from the main memory 101 and transmits the data to the printer 107. In response to this, the printer 107 prints the schema together with the electronic chart.

As described above, in the first embodiment, read-out processing in which an output device (diagnosis support device) that outputs a schematic view (schema) showing a position of a diseased part in a human body structure to an output unit, such as a monitor (display device) or a printing device, also reads out a schematic view to be output from a storage unit is performed. Furthermore, a schematic view that has been read out is selected based on an output format set by a user. Consequently, when there is a plurality of schemata for the same patient, a schema is automatically selected in accordance with the output format; thus, the doctor can output a desired schema to the output unit, such as a display device or a printing device, without performing a troublesome operation.

Also, in the present embodiment, a display format that can be set by a user includes:
  a first output format (static output) according to which an output region is divided, and a plurality of schematic views are simultaneously output, and
  a second output format (dynamic output) according to which a plurality of schematic views are automatically switched at a predetermined timing and sequentially output one-by-one.

Consequently, according to the configuration of the present embodiment, a plurality of schemata can be displayed on an output region whose region is limited in an appropriate manner as desired by the doctor.

Moreover, in the configuration according to the present embodiment, a schematic view related to a diagnostic image selected by a user (a doctor and the like) is read out from the storage unit and output to the output unit. Consequently, according to the configuration of the present embodiment, if a doctor only selects one desired diagnostic image, a plurality of related diagnostic images are automatically selected and output, thereby enabling the doctor to be given appropriate support when examining.

Further, in the configuration of the present embodiment, when receiving the selection of the first output format, the schematic views, the number of which corresponds to a predetermined number of a divided output region, are read out from the storage unit and displayed. Consequently, according to the configuration of the present embodiment, a limited output region of the output unit, such as a display device or a printing device, is optimized so that a plurality of schemata can be displayed therein.

Further still, in the configuration of the present embodiment, when receiving the selection of the second output format, a plurality of schematic views are sequentially output to the output unit in the order of the imaging time. Consequently, according to the configuration of the present embodiment, a doctor can easily grasp the course of a diseased part using a monitor whose output region is limited.

Second Embodiment

In a second embodiment, steps S605, S606, and S902 in a processing procedure in the first embodiment are altered, and the configuration in which a schema is selected based on a patient's history information will be described.

In the first embodiment, in step S605, the selection of a schema related to a diagnostic image displayed on the monitor 104 is received, and the selected schema is displayed. In step S606, the selection of one group in a schema constellation or a plurality of schemata constellations for the same region is received. Then, in step S902, the selection of a combination of a basic schema and layers in date units from a schema image data constellation being dynamically output is received. However, the embodiments of the present invention are not limited to this embodiment. For example, a schema to be read out may be selected based on a patient's history information. Here, a patient's history information is at least one of a diagnosis history, a medication history, and a treatment history.

Figure 10:
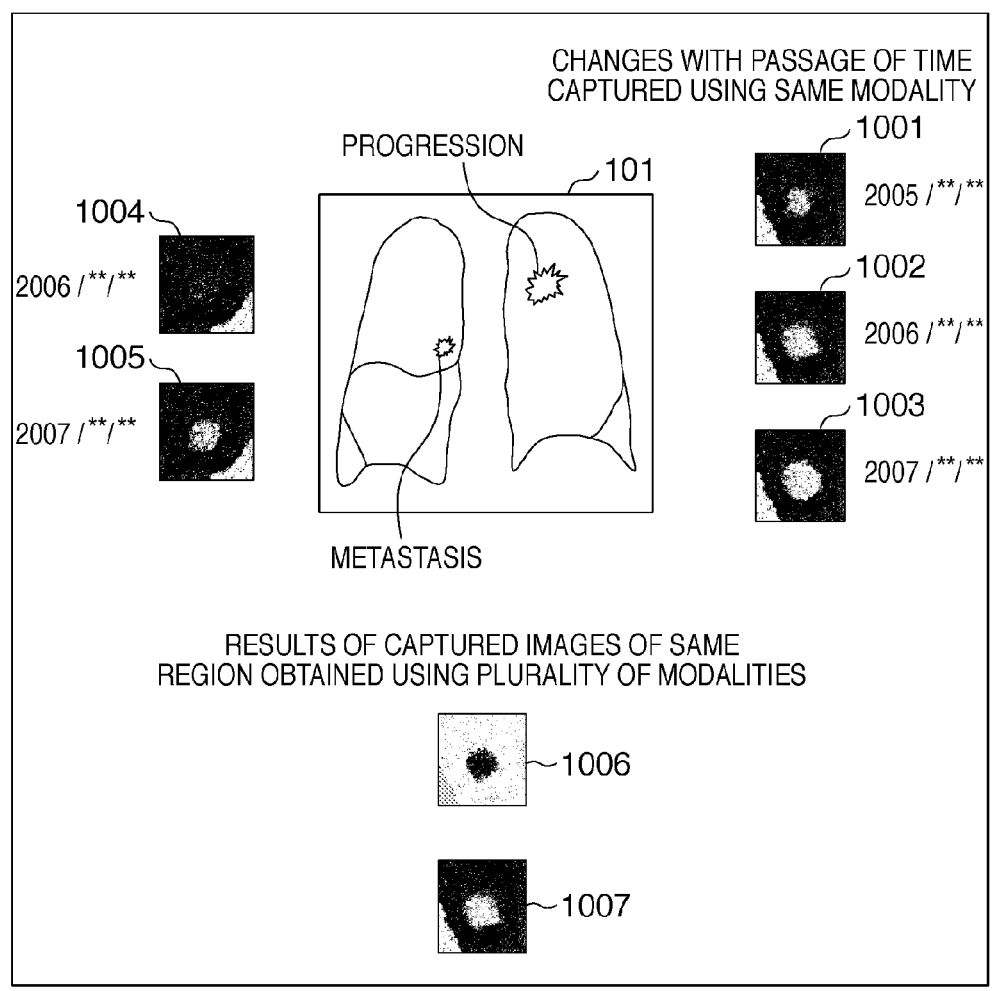
FIG. 10 is a diagram showing an example schema image and example partial region images of diagnostic images that are selected based on a patient's diagnosis history information.

In step S605, when selecting an image based on a diagnosis history, the read-out unit reads out a medical document read in step S202 from the main memory 101, recognizes words recorded on the medical document, and obtains a diagnosis history. For example, in the case of a wait-and-see approach, when detecting a word such as "progress", "spread", "hypertrophy", or "metastasis", it can be determined that a lesion is progressing. Also, when detecting a word, such as "reduction", "recovery", "decrease", it can be determined that a lesion is recovering. Then, when a lesion is progressing, schemata showing the change (if a basic schema is the same, layers showing the change) are selected. Alternatively, when a lesion has metastasized, a schema created before the lesion has metastasized and a schema created after the lesion has metastasized (if the basic schema is the same, layers created then) are selected. Here, as shown in FIG. 10, partial region images 1001 to 1007 of the changing portions in the diagnostic images may be selected and displayed together with a schema. FIG. 10 is a diagram showing an example schema image and example partial region images of diagnostic images selected based on a patient's diagnosis history information. The partial region images of diagnostic images may be the partial region images 1001 to 1005, which are captured using the same modality and show changes with the passage of time, or may be the partial region images 1006 and 1007, which are images of the same portion and captured using a plurality of medical image capturing devices 5.

Figure 11:
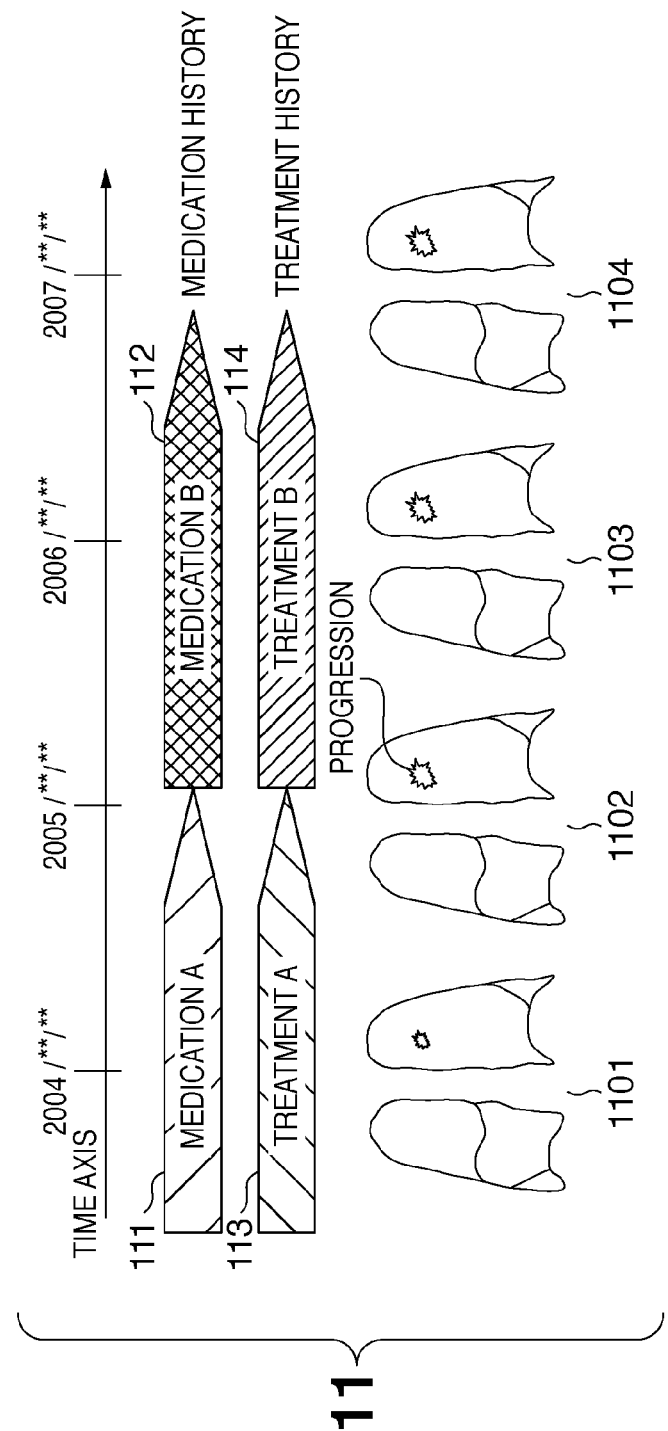
FIG. 11 is a diagram showing example schema images and example partial region images of diagnostic images selected based on information regarding a patient's medication and treatment histories.

Further, when selecting an image based on a medication history and a treatment history, as shown in FIG. 11, the CPU 100 reads out a medical document read in step S202 from the main memory 101, and obtains a patient's medication histories 111 and 112 or treatment histories 113 and 114. FIG. 11 is a diagram showing example schema images and example partial region images of diagnostic images selected based on information regarding a patient's medication history and treatment history. The CPU 100 detects a change in a medication history or a treatment history from history information. Then, the CPU 100 detects a schema created when there is a change in medication history or treatment history from date information, and if there is a schema created when a change was made, a schema 1102 created at that time and schemata 1101 and 1103 created before and thereafter are selected. Further, the type of medicine administered and the treatment methods used before and after the change was made are also displayed on the monitor 104 together with the schemata.

Figure 12:
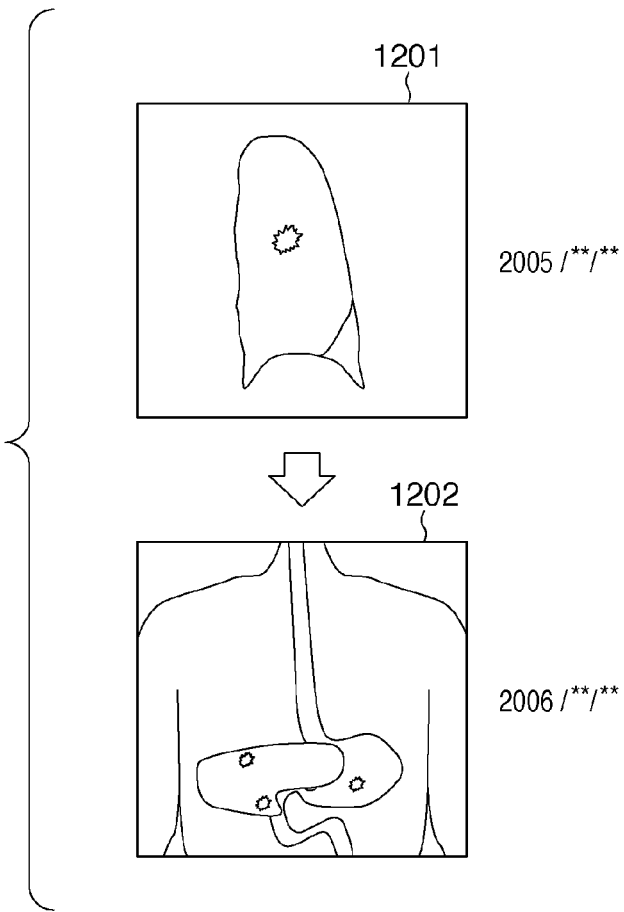
FIG. 12 is a diagram showing example schema images selected based on a patient's diagnosis history information.

In step S606, the CPU 100 may obtain not only a plurality of schemata constellations for the same region, but also a disease name for the region where the disease has been detected. Further, a schema of a region where a possibility of metastasis or a cause-and-effect relationship can be inferred may be selected. At that time, it is desirable that the CPU 100 switches schemata and displays in the order of a cause-and-effect relationship. The order of a cause-and-effect relationship is an order of displaying schemata, for example, in a case where, when a primary tumor is detected in the chest and, thereafter, tumor metastases are detected in the abdomen, as shown in FIG. 12, a schema 1201, on which a tumor in the chest is recorded in detail, is switched to a schema 1202, on which tumor metastases in the abdomen are recorded, so as to display the schema 1202. FIG. 12 is a diagram showing example schema images selected based on a patient's diagnosis history information.

In step S902, also in the case where a schema image data constellation being dynamically output is converted so as to be statically output so that several schemata are selected therefrom, similarly to step S605, a schema is selected based on a patient's history information.

As described above, in the present embodiment, based on a patient's history information stored in the storage unit in association with each schematic view (schema), a schematic view to be read out is determined. Consequently, according to the present embodiment, an appropriate schema can be automatically selected in accordance with a patient's history of disease, which enables a doctor to significantly reduce time and effort. Note that history information includes information indicating at least one of a patient's diagnosis history, medication history, and treatment history.

Further, in the present embodiment, based on such history information, a plurality of schematic views showing a series for the course of a disease are determined to be schematic views to be read out. Consequently, according to the configuration of the present embodiment, a doctor can check the course of a disease of a patient by browsing automatically selected schemata.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

Note that the description of the aforementioned present embodiments is an example of a diagnosis support device according to the present invention, and the present invention is not limited thereto.

As described above, according to the aforementioned configurations, a changing state to be shown on a schematic view is selected, and with a method in accordance with an output format, a method for outputting a changing state regarding a partial region is changed. Consequently, from an image data constellation including a large amount of information, information that a doctor desires can be selected and output.

According to the present invention, a technique with which only a necessary schema can be automatically selected and output from many schemata by performing an easy operation can be provided.

While the present invention has been described with reference to embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-204774, filed on Aug. 7, 2008, which is hereby incorporated by reference herein in its entirety.

What is claimed is:

1. An output device that outputs a schematic view showing a position of a diseased part of a human body, comprising:
at least one processor, and memory, said at least one processor and said memory cooperating to:
read out a plurality of schematic views output from a storage unit adapted to store the schematic views,
select whether to display the plurality of schematic views statically or dynamically, and
output the plurality of schematic views that have been read out to an output unit,
wherein the plurality of schematic views are automatically switched at an arbitrary timing and sequentially output one by one if to display the schematic views dynamically is selected,
wherein the plurality of schematic views are simultaneously output if to display the schematic views statically is selected, and
wherein said at least one processor and said memory cooperate to output the plurality of schematic views in an order of imaging time to the output unit when the second output format is set.

2. The output device according to claim 1, wherein said at least one processor and said memory cooperate to read out a schematic view related to a diagnostic image selected by a user from the storage unit.

3. The output device according to claim 1, wherein said at least one processor and said memory cooperate to read out a number of the schematic views corresponding to a predetermined number of divided output regions from the storage unit when the first output format is set.

4. An output device that outputs a schematic view showing a position of a diseased part of a human body, comprising:
at least one processor, and memory, said at least one processor and said memory cooperating to:
read out a plurality of schematic views output from a storage unit adapted to store the schematic views,
select whether to display the plurality of schematic views statically or dynamically, and
output the plurality of schematic views that have been read out to an output unit,
wherein the plurality of schematic views are automatically switched at an arbitrary timing and sequentially output one by one if to display the schematic views dynamically is selected,
wherein the plurality of schematic views are simultaneously output if to display the schematic views statically is selected, and
wherein said at least one processor and said memory cooperate to select the schematic view to be read out based on a patient's history information stored in the storage unit in association with each of the schematic views.

5. The output device according to claim 4, wherein said at least one processor and said memory cooperate to select a plurality of schematic views showing a series for a course of a disease as the schematic view to be read out based on the history information.

6. The output device according to claim 4, wherein the history information includes information indicating a patient's diagnosis history, medication history, and/or treatment history.

7. The output device according to claim 4, wherein said at least one processor and said memory cooperate to read out a schematic view related to a diagnostic image selected by a user from the storage unit.

8. The output device according to claim 4, wherein said at least one processor and said memory cooperate to read out a number of the schematic views corresponding to a predetermined number of divided output regions from the storage unit when the first output format is set.

9. An output device that outputs a schematic view for use of an electronic chart showing a position of a diseased part of a human body, comprising:
at least one processor, and memory, said at least one processor and said memory cooperating to act as:
a read-out unit adapted to read out a plurality of schematic views, which a doctor has drawn for an identical patient, output from a storage unit adapted to store the schematic views, and
a control unit adapted to dynamically display the plurality of schematic views which have been read out by the read-out unit in a display unit, in the order of the time(s) at which the doctor has drawn respective ones of the schematic views.

10. The output device according to claim 9, wherein said control unit displays the plurality of schematic views in an order of imaging time in the display unit.

11. An output method performed by an output device that outputs a schematic view for use of an electronic chart showing a position of a diseased part of a human body, the method comprising:
a read-out step of reading out a plurality of schematic views, which a doctor has drawn for an identical patient, output from a storage unit adapted to store the schematic views, and
a control step of dynamically displaying the plurality of schematic views read out in the read-out step in a display unit, in the order of the time(s) at which the doctor has drawn respective ones of the schematic views.

12. A non-transitory computer-readable storage medium storing, in executable form, a program for causing a computer to function as an output device that outputs a schematic view for use of an electronic chart showing a position of a diseased part of a human body, by performing:
a read-out step of reading out a plurality of schematic views, which a doctor has drawn for an identical patient, output from a storage unit adapted to store the schematic views, and
a control step of dynamically displaying the plurality of schematic views read out in the read-out step in a display unit, in the order of the time(s) at which the doctor has drawn respective ones of the schematic views.

13. An output device that outputs a schematic view for use of an electronic chart showing a position of a diseased part of a human body, comprising:
    at least one processor, and memory, said at least one processor and said memory cooperating to act as:
    a control unit adapted to dynamically display a plurality of schematic views, which a doctor has drawn for an identical patient, in a display unit, in the order of the time(s) at which the doctor has drawn respective ones of the schematic views, and
    a print unit adapted to print the plurality of schematic views dynamically displayed in the display unit by statically expanding the schematic views.

14. An output method performed by an output device that outputs a schematic view for use of an electronic chart showing a position of a diseased part of a human body, the method comprising:
    a control step of dynamically displaying a plurality of schematic views, which a doctor has drawn for an identical patient, in a display unit, in the order of the time(s) at which the doctor has drawn respective ones of the schematic views, and
    a printing step of printing the plurality of schematic views dynamically displayed in the display unit by statically expanding the schematic views.

15. A non-transitory computer-readable storage medium storing, in executable form, a program for causing a computer to function as an output device that outputs a schematic view for use of an electronic chart showing a position of a diseased part of a human body, by performing:
    a control step of dynamically displaying a plurality of schematic views, which a doctor has drawn for an identical patient, in a display unit, in the order of the time(s) at which the doctor has drawn respective ones of the schematic views, and
    a printing step of printing the plurality of schematic views dynamically displayed in the display unit by statically expanding the schematic views.

16. An output device that outputs a schematic view for use of an electronic chart showing a position of a diseased part of a human body, comprising:
    at least one processor, and memory, said at least one processor and said memory cooperating to act as:
    a read-out unit adapted to read out a plurality of schematic views to which lesion information has been added; and
    a control unit adapted to dynamically display the plurality of schematic views which have been read out using by the read-out unit in a display unit based on a time when lesion information is added to a schematic view.

17. An output method performed by an output device that outputs a schematic view for use of an electronic chart showing a position of a diseased part of a human body, the method comprising the steps of:
    reading out a plurality of schematic views to which lesion information has been added; and
    dynamically displaying the plurality of schematic views which have been read out in the step of reading out in a display unit based on a time when lesion information is added to a schematic view.

18. A non-transitory computer-readable storage medium storing, in executable form, a program for causing a computer to function as an output device that outputs a schematic view for use of an electronic chart showing a position of a diseased part of a human body, by performing the steps of:
    reading out a plurality of schematic views to which lesion information has been added; and
    dynamically displaying the plurality of schematic views which have been read out in the step of reading out in a display unit based on a time when lesion information is added to a schematic view.

\* \* \* \* \*